United States Patent [19]

Chikama

[11] Patent Number: 4,601,283
[45] Date of Patent: Jul. 22, 1986

[54] ENDOSCOPE WITH A MEMORY SHAPE ALLOY TO CONTROL TUBE BENDING

[75] Inventor: Toshio Chikama, Tokyo, Japan

[73] Assignee: Machida Endoscope Co., Ltd., Tokyo, Japan

[21] Appl. No.: 452,377

[22] Filed: Dec. 22, 1982

[30] Foreign Application Priority Data

Dec. 29, 1981 [JP] Japan ............................ 56-195770[U]

[51] Int. Cl.$^4$ ............................................... A61B 1/06
[52] U.S. Cl. ........................................................ 128/4
[58] Field of Search ........................................ 128/4-8, 128/785, 657

[56] References Cited

U.S. PATENT DOCUMENTS

| | | | |
|---|---|---|---|
| 3,452,742 | 7/1969 | Muller | 128/657 |
| 3,890,977 | 6/1975 | Wilson | 128/785 |
| 4,182,547 | 1/1980 | Siegmund | 128/4 |
| 4,351,323 | 9/1982 | Ouchi et al. | 128/4 |

Primary Examiner—Edward M. Coven
Assistant Examiner—Max F. Hindenburg
Attorney, Agent, or Firm—Peter L. Berger

[57] ABSTRACT

Disclosed is an endoscope having a long flexible image guide, such as a colon endoscope, in which a shape memory alloy is built in a flexible tube in which the image guide is inserted. When the flexible tube is inserted in the deep portion of a complicatedly bent organ such as the colon, the flexible tube which is partially bent according to the bending of the colon or the like is straightened by utilizing the restoring property of the shape memory alloy to straighten the correspondingly bent portion of the colon or the like, whereby the flexible tube can easily be inserted in the complicatedly bent portion of the colon or the like while straightening this portion.

7 Claims, 11 Drawing Figures

PRIOR ART
FIG.1(I)
PRIOR ART
FIG.1(II)
PRIOR ART
FIG.1(III)
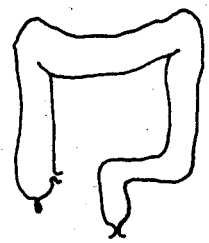
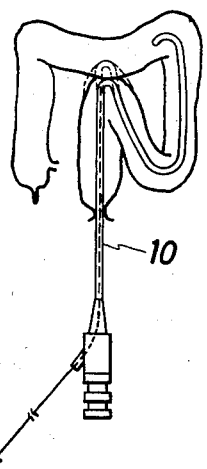
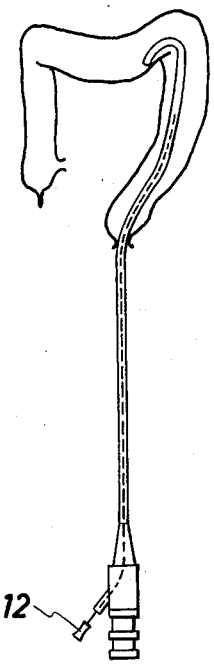

FIG. 2
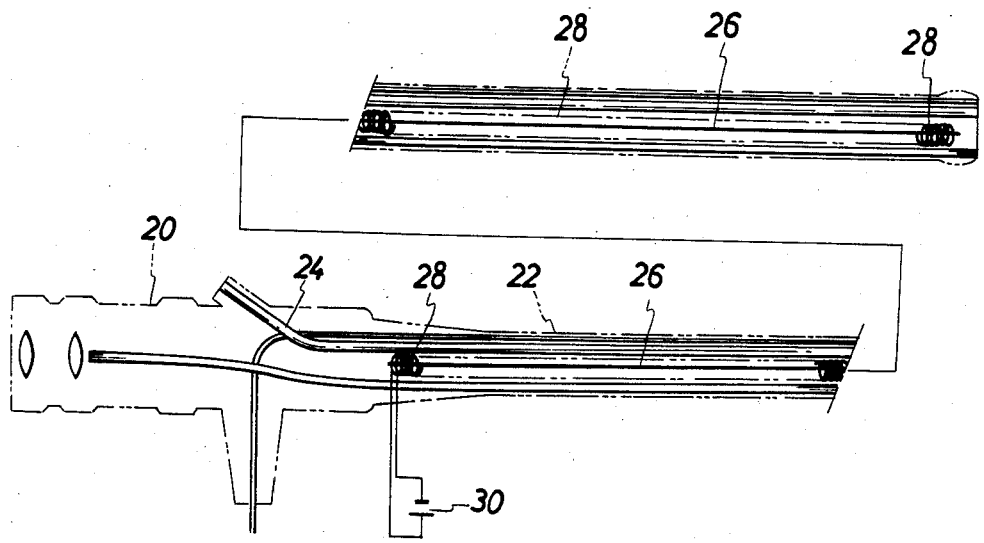
FIG.3(I)    FIG.3(II)    FIG.3(III)    FIG.3(IV)
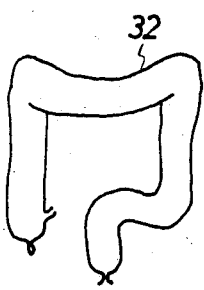 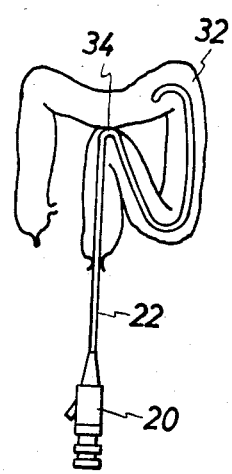 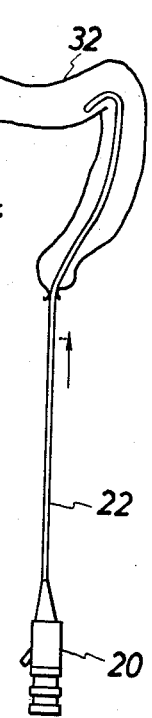 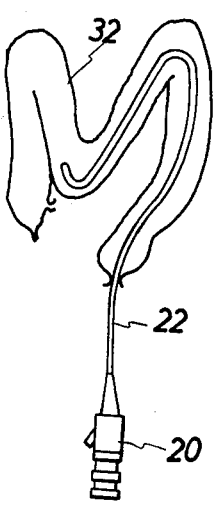

ENDOSCOPE WITH A MEMORY SHAPE ALLOY TO CONTROL TUBE BENDING

BACKGROUND OF THE INVENTION

(1) Field of the Invention

The present invention relates to a structure of a flexible tube of an endoscope which is used in the medical and industrial fields. More particularly, the present invention relates to a technique, according to which a shape memory alloy is built in a flexible tube and the flexible tube is inserted into a complicatedly bent portion while straightening the bent portion by utilizing the restoring property of the shape memory alloy according to need.

(2) Description of the Prior Art

When the interior of the colon is observed by using an endoscope having a long flexible tube, such as a colon endoscope, it is very difficult to insert a flexible tube 10 into the complicatedly bent, long colon, as shown in FIG. 1-(I), because the tube 10 can hardly be advanced in the bent portion. Accordingly, there is ordinarily adopted a method in which, as shown in FIG. 1-(III), a stylet 12 composed of an elastic material such as a piano wire is inserted into or withadrawn from the flexible tube 10 to straighten the bent portion of the colon and the flexible tube is thus inserted little by little. However, when the stylet 12 is going to be inserted into the bent portion of the flexible tube 10 as shown in FIG. 1-(II), the stylet 12 merely presses the bent portion of the flexible tube 10 but the stylet 12 cannot be inserted into the flexible tube 10, with the result that the flexible tube cannot be straightened. If it is intended to forcibly insert the stylet 12 into the flexible tube 10, there arises a risk of breakage of the flexible tube 10. However, if the stylet 12 is not inserted into the bent portion, the bent portion cannot be straightened. Accordingly, the conventional method is technically contradictory, and the observation of the colon or the like with an endoscope involves serious difficulties.

It may be considered that good results will be obtained if the stylet is inserted into the flexible tube in advance and the flexible tube is inserted into the bent portion. However, in this case, the flexibility is lost in the stylet-inserted flexible tube and insertion of the flexible tube into the bent portion becomes impossible.

Accordingly, the success in the observation of the colon or the like with an endoscope has heretofore depended on the skill and experience of an operator.

SUMMARY OF THE INVENTION

The present invention relates to an endoscope having a shape memory alloy built in a flexible tube, in which on insertion of the flexible tube of the endoscope into the interior of an organ such as the colon, the flexible tube is advanced and inserted to the deep portion to be oberved while repeating the operations of passing the flexible tube through a complicatedly bent portion, straightening the bent portion by utilizing the restoring property of the shape memory alloy and inserting the flexible tube through the straightened portion. It is a primary object of the present invention to easily insert a flexible tube of an endoscope into a complicatedly bent, long organ without using an auxiliary member such as a stylet by building a shape memory alloy in the flexible tube. Another object of the present invention to increase the insertion adaptability of the flexible tube by partially straightening the shape memory alloy.

BRIEF DESCRIPTION OF THE DRAWINGS

FIG. 1 is a diagram illustrating the states of use of a conventional endoscope.

FIG. 2 is a diagram illustrating a first embodiment of the present invention.

FIG. 3 is a diagram illustrating the states of use of the endoscope according to the present invention.

DETAILED DESCRIPTION OF THE INVENTION

Figure 4:
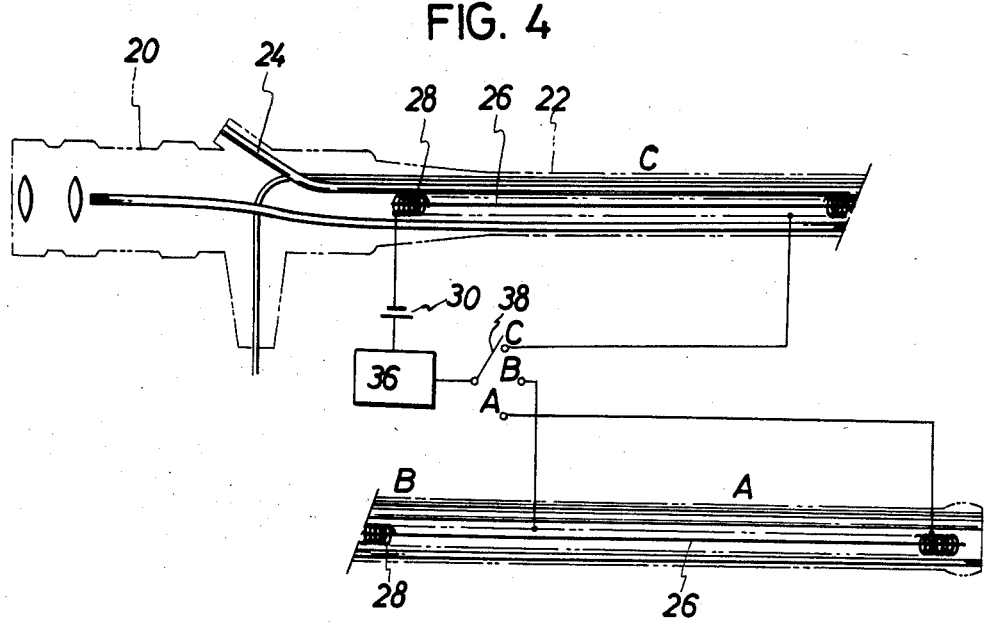
FIG. 4 is a diagram illustrating a second embodiment of the present invention.

Recently, alloys called "shape memory alloys" have been developed. More specifically, if a certain alloy is shaped and heat-treated, it exerts an effect of memorizing this shape. If a force is applied to this alloy at a certain temperature lower than the transformation point thereof, the shape of the alloy is changed, but if the alloy is heated to the transformation point of the alloy, it instantaneously restores its original shape. For example, when a straight shape is memorized in the alloy and it is then bent, if the alloy is heated to the deformation point, the original straight shape is instantaneously restored. This transformation point may be adjusted by the alloy composition or heat treatment. For example, a high temperature or such a low temperature as not observed under ordinary weather conditions can be set as the transformation point. As the shape memory alloy having such properties, there can be mentioned, for example, a gold/cadmium alloy, a copper/zinc alloy, a nickel/aluminum alloy and a nickel/titanium alloy.

At temperatures other than the transformation point, the shape memory alloy is very soft and it resembles lead in that if it is bent, the bent shape is retained. When the temperature is changed to the transformation point, the memorized shape is restored by a strong spring property.

The present invention is directed to a technique of increasing the insertion adaptability of an endoscope by building a shape memory alloy in the endoscope. Members to be built in the endoscope differ according to the intended use of the endoscope. Ordinarily, however, such members as an image guide, a light guide, an angle operating portion for bending a bendable top end portion and a forceps inserting tube are built in the endoscope. Since the present invention has no direct relation to these members, explanation of these members is omitted.

FIG. 2 is a diagram illustrating a first embodiment of the present invention. Reference numerals 20, 22, 24 and 26 represent a handle of the endoscope, a flexible tube of the endoscope, a forceps inserting tube and a shape memory alloy arranged in the flexible tube 22, respectively. A heating wire 28 such as a nichrome wire is arranged as the transformation temperature-imparting medium means around the shape memory alloy 26 through an insulating member (not shown). Reference numeral 30 represents a power source.

In the case where a memory shape alloy in which a straight shape is memorized is used as the alloy 26, when the endoscope is going to be inserted into a bent organ 32 as shown in FIG. 3-(I), if it is intended to press the endoscope into the organ 32, the bent portion 34 of the flexible tube 22 is further bent in the bending direction as shown in FIG. 3-(II). The organ is deformed but insertion is not advanced, which sometimes results in damage on the inner wall of the organ. In this case, the temperature of the shape memory alloy is changed to the transformation point by heating wire 28, and at this moment, the original straight shape is restored in the shape memory alloy and the alloy becomes rigid. Therefore, the organ 32 is deformed as shown in FIG. 3-(III) and further insertion of the endoscope becomes possible. With lowering of the temperature of the heating wire 28, the alloy becomes soft again and the original state is restored in the organ, as shown in FIG.3-(IV).

When the foregoing operations are repeated, the flexible part 22 can be inserted little by little into the deep portion of the organ.

In the foregoing embodiment, the heating wire is used as the temperature medium for changing the temperature to the transformation point. A soft cylindrical heating tube having a shape memory alloy arranged therein through an insulating member may be used instead of the above heating wire, or there may be adopted a method in which an electric current is supplied to the shape memory alloy per se to produce the transformation temperature. Furthermore, there may be adopted a method in which a tube is wound around the shape memory alloy and a warm liquid is passed through the tube to heat the shape memory alloy to the transformation point thereof. Moreover, there may be adopted a method in which the transformation temperature is adjusted to a low level and transformation is caused by circulation of cold water.

FIG. 4 illustrates a second embodiment of the present invention, in which the transformation temperature is not applied to the entire length of the shape memory alloy but is applied only partially to the shape memory alloy. In the case where a heating wire is used as the transformation temperature-imparting medium means, this heating wire 28 is divided into a number of blocks A through C. In FIG. 4, reference numerals 30, 36 and 38 represent a power source, a constant current device and a changeover switch, respectively, and connecting lines from the respective blocks are connected to the changeover switch 38.

In this embodiment, if the changeover switch 38 is connected to the block A, the transformation temperature is brought about in the blocks A through C and the shape memory alloy 26 in these blocks A through C becomes rigid and the original shape is restored. If the changeover switch 36 is connected to the block B, the shape memory alloy in the blocks B and C becomes rigid and the original shape is restored in the blocks B and C. If the changeover switch is connected to the block C, the shape memory alloy in the block C becomes rigid and the original shape is restored in the block C.

Figure 5:
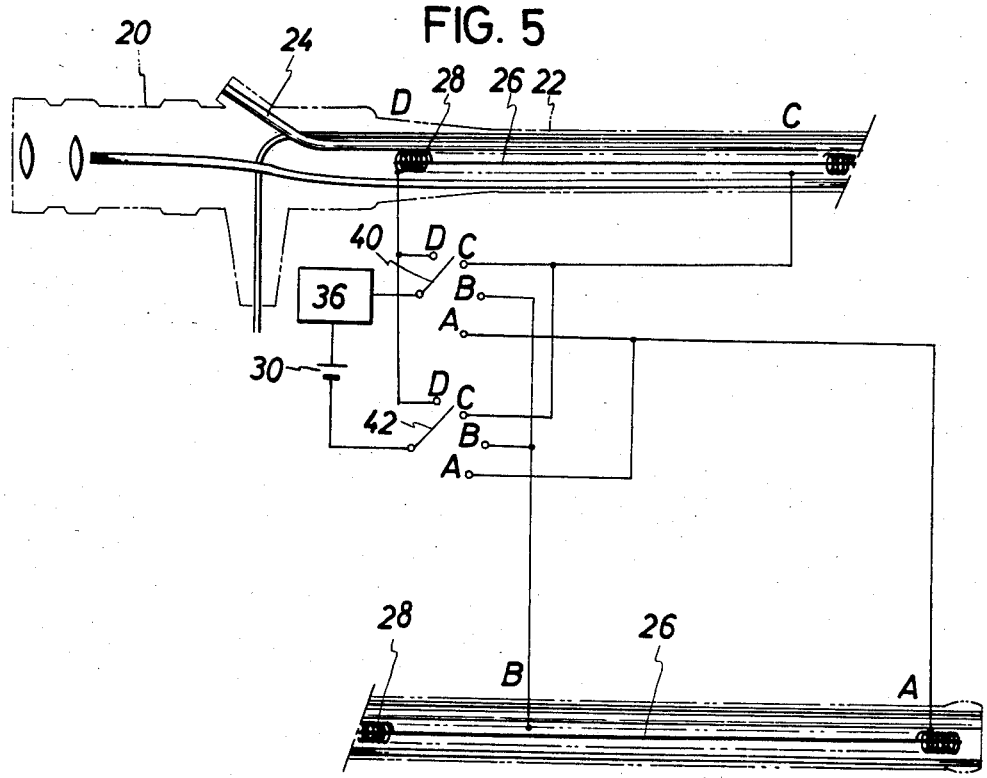
FIG. 5 is a diagram illustrating a third embodiment of the present invention.

FIG. 5 illustrates a third embodiment, in which the transformation temperature is given partially to the shape memory alloy. In the case where a heating wire is used as the transformation temperature-imparting medium means, the heating wire is divided into an optional number of blocks A through D. In FIG. 5, reference numerals 30 and 36 represent a power source and a constant current device, respectively, and each of reference numerals 40 and 42 represents a changeover switch and connecting lines from the respective blocks are connected to both the changeover switches 40 and 42.

In this embodiment, if the changeover switch 42 is connected to the block A and the changeover switch 40 is connected to the block B, the transformation temperature is given to the shape memory alloy 26 in the blocks A and B, and the alloy 26 becomes rigid in the blocks A and B and the original shape is restored in the blocks A and B. If the changeover switch 42 is kept connected to the block 42 and the changeover switch 40 is connected to the block C, the transformation temperature is given to the shape memory alloy in the region of the blocks A through C, and if the changeover switch 42 is kept connected to the block A and the changeover switch 40 is connected to the changeover switch 40, the transformation temperature is given to the shape memory alloy in the region of blocks A through D, that is, along the entire length of the alloy.

If the changeover switch 42 is connected to the block B and the changeover switch 40 is connected to the block C, the transformation temperature is given to the shape memory alloy in the region of the blocks B and C and the alloy is made rigid only in this region. If the changeover switch 42 is kept connected to the block B and the changeover switch 40 is connected to the block D, the transformation temperature is given to the memory shape alloy in the region of blocks B through D, and if the changeover switch 42 is connected to the block C and the changeover switch 40 is connected to the block D, the transformation temperature can be given to the shape memory alloy only in the region of the blocks C and D.

In this embodiment, as is seen from the foregoing description, the shape memory alloy can be made rigid selectively in the portion corresponding to the activated blocks of the heating wire. Accordingly, when the endoscope is inserted into an organ, the desired portion of the flexible tube can be made rigid according to the bending state of the organ, and handling of the endoscope can further be facilitated.

Figure 6:
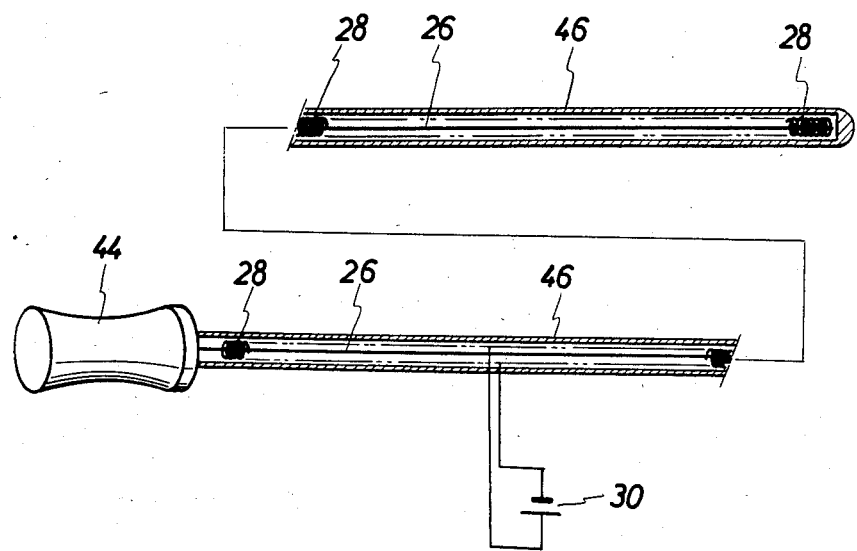
FIG. 6 is a diagram illustrating a fourth embodiment of the present invention.

FIG. 6 illustrates a fourth embodiment of the present invention, in which the shape memory alloy and the transformation temperature-imparting medium means are not built in the endoscope but are arranged dismountably from the endoscope. In this embodiment, a heating wire 28 as the transformation temperature-imparting medium means is disposed around the shape memory alloy, and the combination of the shape memory alloy and the heating wire may be any of the combinations shown in the foregoing embodiments. An electrically conductive tube or a warm liquid circulated through a tube may be used as the transformation temperature-imparting medium means instead of the heating wire. In FIG. 6, reference numeral 44 represents a handle for supporting the shape memory alloy 26, reference numeral 46 represents an outer flexible cover tube for covering the shape memory alloy and transformation temperature-imparting medium means, such as a spiral wire tube or a synthetic resin tube. Reference numeral 30 represents a power source, which may be arranged in the same manner as in the above-mentioned second or third embodiment.

If the structure of this embodiment is adopted, the operation can be performed through the handle 44 while inserting the shape memory alloy and transformation temperature-imparting medium means into the forceps inserting tube 24 arranged in the endoscope. In the case where an independent channel different from the forceps-inserting tube is provided, this channel may be utilized for the operation.

In each of the foregoing embodiments, the memorized shape is a straight shape. Of course, in the present invention, any appropriate memorized shape may be set according to the intended use of the endoscope.

In each of the foregoing embodiments, one shape memory alloy is employed. However, in the present invention, there may be adopted a modification in which two shape memory alloys having memorized shapes reverse to each other are arranged in combination and the transformation temperature-imparting medium means is disposed so that they are independently operated. In this modification, the flexible tube can be bent and straightened in optional directions.

Various advantages can be attained when the endoscope of the present invention having the above-mentioned structural and functional features is used. For example, when the flexible tube is inserted into a complicately bent organ such as the colon, the flexible tube can be passed through the bent portion while straightening the bent portion of the flexible tube and insertion can be accomplished very easily without any skill or experience. Namely, the bent organ can be deformed together with the endoscope by utilizing the solidification and shape-restoring force of the shape memory alloy built or inserted in the endoscope, and the endoscope is gradually inserted into the organ very smoothly.

Furthermore, in the case where an industrial endoscope is to be inserted into a material in which the bent state is known, a shape corresponding to the bent state is memorized in the shape memory alloy and the transformation temperature is given according to need, whereby insertion is facilitated.

What is claimed is

1. An endoscope having a flexible tube and a handle, an improvement comprising a shape memory alloy and a transformation temperature-imparting medium means, said shape memory alloy and transformation temperature-imparting medium means being accommodated in the flexible tube, said shape memory alloy being selectively made rigid under control of said transformation temperature-imparting medium means to restore a shape memorized by the shape memory alloy and to control the deformation of the flexible tube, said transformation temperature-imparting medium means comprising means to divide said flexible tube and said accommodated shape memory alloy into a plurality of longitudinal sections and to independently selectively actuate selected ones of said longitudinal sections.

2. An endoscope as set forth in claim 1, wherein said shape memory alloy comprises a plurality of shape memory alloys having different memorized shapes, said plurality of shape memory alloys arranged to be independently actuated by the transformation temperature-imparting medium means.

3. An endoscope as set forth in claim 1, wherein said shape memory alloy and temperature imparting medium are built into said flexible tube.

4. An endoscope as set forth in claim 1, wherein said shape memory alloy and temperature-imparting medium are inserted into said flexible tube.

5. An endoscope as set forth in claim 1, wherein said means to divide said flexible tube into a plurality of longitudinal segments comprises a heating wire divided into a plurality of separate segments with electrical power separately supplied to each of said segments to separately control the shape memory alloy accommodated in each longitudinal section of said flexible tube.

6. An endoscope as set forth in claim 5, further comprising a switch means to control the location where said shape memory alloy is to receive said electrical power.

7. An endoscope as set forth in claim 6, wherein said switch means controls the supply of electrical power to be cumulative along said flexible tube such that sequential segments are sequentially controllably deformed.

* * * * *